(12) United States Patent
Zasloff

(10) Patent No.: US 9,393,447 B2
(45) Date of Patent: Jul. 19, 2016

(54) LIQUID NON-IONIC SALT-FREE SKIN AND HAIR TREATMENT COMPOSITION THAT CONTAINS LAUROYL N-METHYL GLUCAMIDE

(71) Applicant: Formula XO, Inc., Arlington, VA (US)

(72) Inventor: Michael Zasloff, Merion, PA (US)

(73) Assignee: Formula XO, Inc., Arlington, VA (US)

( * ) Notice: Subject to any disclaimer, the term of this patent is extended or adjusted under 35 U.S.C. 154(b) by 0 days.

(21) Appl. No.: 14/172,667

(22) Filed: Feb. 4, 2014

(65) Prior Publication Data

US 2014/0242018 A1 Aug. 28, 2014

Related U.S. Application Data

(60) Provisional application No. 61/760,839, filed on Feb. 5, 2013.

(51) Int. Cl.
| | | |
|---|---|---|
| *A61K 8/42* | (2006.01) | |
| *A61Q 5/02* | (2006.01) | |
| *A61K 47/26* | (2006.01) | |
| *A61K 8/60* | (2006.01) | |
| *A61K 31/197* | (2006.01) | |
| *A61K 9/00* | (2006.01) | |
| *A61K 8/44* | (2006.01) | |
| *A61Q 19/10* | (2006.01) | |
| *A61K 31/164* | (2006.01) | |
| *A61K 31/7004* | (2006.01) | |

(52) U.S. Cl.
CPC ... *A61Q 5/02* (2013.01); *A61K 8/44* (2013.01); *A61K 8/604* (2013.01); *A61K 9/0014* (2013.01); *A61K 31/164* (2013.01); *A61K 31/7004* (2013.01); *A61K 47/26* (2013.01); *A61Q 19/10* (2013.01); *A61K 2800/596* (2013.01)

(58) Field of Classification Search
CPC ... A61K 47/26; A61K 9/0014; A61K 31/164; A61K 31/7004; A61K 8/604; A61K 2800/596; A61K 8/44; A61K 2300/00; A61Q 5/02; A61Q 19/10

See application file for complete search history.

(56) References Cited

U.S. PATENT DOCUMENTS

| | | |
|---|---|---|
| 4,154,706 A | 5/1979 | Kenkare et al. |
| 5,009,814 A | 4/1991 | Kelkenberg et al. |
| 5,174,927 A | 12/1992 | Honsa |
| 5,183,601 A | 2/1993 | Jisai et al. |
| 5,266,690 A | 11/1993 | McCurry, Jr. et al. |
| 5,308,526 A | 5/1994 | Dias et al. |
| 5,788,992 A | 8/1998 | Mahieu et al. |
| 6,395,258 B1 | 5/2002 | Steer |
| 7,084,104 B2 | 8/2006 | Martin et al. |
| 2006/0178288 A1 | 8/2006 | Albrecht et al. |
| 2008/0113891 A1 | 5/2008 | Arsharuni et al. |
| 2009/0200511 A1 | 8/2009 | Allen et al. |
| 2009/0304620 A1 | 12/2009 | Schulze zur Wiesche et al. |
| 2011/0124543 A1 | 5/2011 | Lutrario et al. |

FOREIGN PATENT DOCUMENTS

EP 0550656 B1 7/1993

OTHER PUBLICATIONS

International Search Report and Written Opinion Issued by the U.S. Patent and Trademark Office as International Searching Authority for International Application No. PCT/US14/14693 mailed May 19, 2014 (11 pgs.).

*Primary Examiner* — Ali Soroush
*Assistant Examiner* — Genevieve S Alley
(74) *Attorney, Agent, or Firm* — Wilmer Cutler Pickering Hale and Dorr LLP

(57) ABSTRACT

Compositions and methods for their use in treating human or other mammalian skin and hair. Non-ionic, salt-free non-solidifying formulations of Lauroyl N methyl glucamide and alkyl glycosides are disclosed that impart beneficial barrier properties to skin and hair.

9 Claims, 2 Drawing Sheets

LIQUID NON-IONIC SALT-FREE SKIN AND HAIR TREATMENT COMPOSITION THAT CONTAINS LAUROYL N-METHYL GLUCAMIDE

REFERENCE TO RELATED APPLICATIONS

This application claims the benefit of priority under 35 U.S.C. §119(e) to U.S. application Ser. No. 61/760,839, filed on Feb. 5, 2013, the contents of which are incorporated in their entirety by reference.

FIELD OF THE INVENTION

This invention relates to methods of formulating Lauryl N-Methyl Glucamide for hair and skin applications. The method comprises formulating Lauryl N-Methyl Glucamide to achieve a non-solidifying water soluble formulation that exhibits unanticipated physical properties of a nature beneficial to its application to skin surfaces or hair.

BACKGROUND OF THE INVENTION

Lauroyl N-Methyl Glucamide (D-glucitol, 1-deoxy-1-(methylamino)-, N—C10-16 acyl derivatives CAS#173145-38-5) has the structure indicated below.

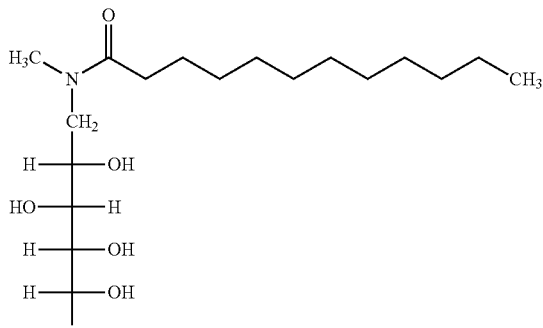

Lauryl N-Methyl Glucamide ("LMG")

Lauroyl N-Methyl Glucamide ("LMG") as described in this invention is generally a mixture consisting of $C_{10}$, $C_{12}$, $C_{14}$, $C_{16}$ acyl compounds. It is a waxy, non-oily solid that melts at about 60° C. in water. Solutions of LMG solidify into hard non-oily gels at temperatures of about 35° that resemble agar gels in feel and consistency. LMG is a member of the group of chemical compounds referenced to as alkyl N-Methyl glucamides or alternatively as alkanoyl N-Methyl glucamides.

LMG-containing formulations are known to form rigid solid gels at temperatures below 10° C.; therefore, the resulting solids must be subsequently warmed to temperatures above ambient conditions (21° C.) to restore a liquid solution. Alkyl N-Methyl glucamides have been incorporated into hair products such as mousses and shampoos (U.S. Pat. No. 6,395,258) because of the thickness (viscosity) they impart. However, the formulations disclosed (such as those described in U.S. Pat. No. 6,395,258) solidify at temperatures between 15°-20° C. (See Example 1), which is an unacceptable property when such phase transitions are not permitted in a commercial product. LMG also has been used in liquid laundry and dishwashing detergents (U.S. Pat. No. 5,332,538). These detergents contain high concentrations of strong anionic detergents, which both provide the detergency required for the intended use of the product, and secondarily prevent LMG from solidification. An example of a liquid detergent formulation is disclosed in U.S. Pat. No. 5,174,927:

TABLE 1

| INGREDIENT | Wt. % |
|---|---|
| Coconutalkyl ($C_{12}$) N-methyl glucamide | 14 |
| $C_{14-15}$ EO (2.25) sulfate, Na salt | 10.0 |
| $C_{14-15}$ EO (7) | 4.0 |
| $C_{12-14}$ alkenylsuccinic anhydride[1] | 4.0 |
| $C_{12-14}$ fatty acid* | 3.0 |
| Citric acid (anhydrous) | 4.6 |
| Protease (enzyme)[2] | 0.37 |
| Termamyl (enzyme)[3] | 0.12 |
| Lipolase (enzyme)[4] | 0.36 |
| Carezyme (enzyme)[5] | 0.12 |
| Dequest 2060S[6] | 1.0 |
| NaOH (pH to 7.6) | 5.5 |
| 1,2 propanediol | 4.7 |
| Ethanol | 4.0 |
| Sodium metaborate | 4.0 |
| $CaCl_2$ | 0.014 |
| Ethoxylated tetraethylene pentamine[7] | 0.4 |
| Brightener[8] | 0.13 |
| Silane[9] | 0.04 |
| Soil release polymer[10] | 0.2 |
| Silicone (suds control)[11] | 0.4 |
| Silicone dispersant[12] | 0.2 |
| Water and minors | Balance |

LMG has been used to increase the viscosity of cleansing compositions. U.S. Pat. No. 5,009,814 describes addition of LMG for the use in shampoo. The formulation contains a strong anionic detergent that provides the required cleansing activity, and the specified concentration secondarily prevents LMG from solidifying.

TABLE 2

Shampoo formulations based on a paraffinsulfonic acid sodium salt or a paraffinsulfonic acid glucamine salt (which is gentle to skin), in combination with mixtures of thickeners

| Formula | I (%) | II (%) | III (%) |
|---|---|---|---|
| Paraffinsulfonic acid, glucamine salt | 13.5 | 13.5 | 13.5 |
| Marlamid ® (coconut oil fatty acid diethanolamide | | 3.0 | |
| N-methyl coconut oil fatty acid glucamide | | | 3.0 |
| Antil ® (Polyoxyethylene-propylene glycol dioleate | 2.56 | 2.56 | 2.56 |
| Viscosity (mPa · S) | 142 | 317 | 1,590 |
| Paraffinsulfonic acid, sodium salt | 13.5 | 13.5 | 13.5 |
| Marlamid ® | | 3.0 | |
| N-methyl coconut oil fatty acid glucamide | | | 3.0 |
| Antil ® | 2.56 | 156 | 2.56 |
| Viscosity (mPa · S) | 63 | 217 | 622 |

It would be advantageous for the purpose of skin and hair treatments, such as a shampoo or skin cleanser/hydrating lotions to create an aqueous formulation of LMG which is free of strong anionic detergents (which are damaging to both skin and hair) and which remain liquid at temperatures that would be experienced during storage and shipping.

SUMMARY OF THE INVENTION

The present invention is directed to a simple method of formulating LMG for the purpose of its use on hair and skin surfaces as a non-solidifying liquid shampoo, or skin cleanser/hydrating lotion without the addition of ionic detergents or salts. In one embodiment the method comprises the formulation of LMG with decyl glucoside in such proportions that LMG does not solidify (remains liquid) at room temperature or below (21° C.). The addition of certain simple low molecular weight compounds in the correct proportions to LMG can prevent the liquid to solid phase transition. Furthermore, these LMG compositions still retain the capacity to create a non-oily water impermeable barrier when applied to skin or hair.

In another embodiment, the formulation includes glycerol in addition to water and LMG.

In yet another embodiment of the invention, the formulation includes other components required to exhibit certain properties, such as viscosity enhancers, fragrances, conditioners, antibacterial agents, colorants, preservatives, silicones, anti-frizz agents.

In certain embodiments of the invention, the formulation contains LMG at a concentration between 0.5% and 30% wt/wt and decyl glucoside at a concentration between 0.5% and 60% wt/wt, with the weight ratio of the two compounds (LMG to decyl glucoside) of between 2:1 and 1:3, and which remains liquid at temperatures below 0° C.

In certain embodiments of the invention, the formulation contains LMG at a concentration between 0.5% and 30% wt/wt and decyl glucoside at a concentration between 0.5% and 30% wt/wt, with the weight ratio of the two compounds (LMG to decyl glucoside) of between 2:1 and 1:1, and which remains liquid at temperatures below 0° C.

In particular, a preferred embodiment of the invention is a formulation that contains LMG at a concentration of between 5-15% wt/wt, e.g., about 14% wt/wt, decyl glucoside at a concentration between 20% and 30% wt/wt and glycerol at about 12% wt/wt and which remains liquid at temperatures below 0° C.

In another embodiment, a formulation contains LMG at a concentration of between 5-15% wt/wt, e.g., about 10% wt/wt, decyl glucoside at a concentration between 5-10% wt/wt, and glycerol at 10% wt/wt, and which remains liquid at temperatures below 0° C.

A second preferred embodiment of the invention is a formulation that contains LMG at a concentration of about 3% wt/wt, decyl glucoside between 3-8% wt/wt, glycerol at 17% wt/wt, and which remains liquid at temperatures below 0° C.

In certain embodiments, the formulation can include LMG at concentrations of 0.5-1.0 wt %, 1-2 wt %, 2-3 wt %, 3-4 wt %, 4-5 wt %, 5-6 wt %, 6-7 wt %, 7-8 wt %, 8-9 wt %, 9-10 wt %, 10-11 wt %, 11-12 wt %, 12-13 wt %, 13-14 wt %, 14-15 wt %, 15-16 wt %, 16-17 wt %, 17-18 wt %, 18-19 wt %, 19-20 wt %, 20-21 wt %, 21-22 wt %, 22-23 wt %, 23-24 wt %, 24-25 wt %, 25-26 wt %, 26-27 wt %, 27-28 wt %, 28-29 wt % or 29-30 wt %, or any combination thereof.

In certain embodiments, the formulation can include decyl glucoside at concentrations of 0.5-1.0 wt %, 1-2 wt %, 2-3 wt %, 3-4 wt %, 4-5 wt %, 5-6 wt %, 6-7 wt %, 7-8 wt %, 8-9 wt %, 9-10 wt %, 10-11 wt %, 11-12 wt %, 12-13 wt %, 13-14 wt %, 14-15 wt %, 15-16 wt %, 16-17 wt %, 17-18 wt %, 18-19 wt %, 19-20 wt %, 20-21 wt %, 21-22 wt %, 22-23 wt %, 23-24 wt %, 24-25 wt %, 25-26 wt %, 26-27 wt %, 27-28 wt %, 28-29 wt % or 29-30 wt %, in combination with LMG at concentrations of 0.5-1.0 wt %, 1-2 wt %, 2-3 wt %, 3-4 wt %, 4-5 wt %, 5-6 wt %, 6-7 wt %, 7-8 wt %, 8-9 wt %, 9-10 wt %, 10-11 wt %, 11-12 wt %, 12-13 wt %, 13-14 wt %, 14-15 wt %, 15-16 wt %, 16-17 wt %, 17-18 wt %, 18-19 wt %, 19-20 wt %, 20-21 wt %, 21-22 wt %, 22-23 wt %, 23-24 wt %, 24-25 wt %, 25-26 wt %, 26-27 wt %, 27-28 wt %, 28-29 wt % or 29-30 wt %, in any combination.

In place of decyl glucoside other alkyl glycosides can be substituted. Such surfactants include but are not limited to one or more sugar-based surfactants, i.e. alkyl polyglycosides. The alkyl polyglycosides have the formula (II) or Formula (III) below:

wherein $R_1$ is a monovalent organic radical having from about 6 to about 30 carbon atoms, preferably from 6 to 12 carbon atoms, and more preferably having an average of from 10 to 10.5 carbon atoms; Z is saccharide residue having 5 or 6 carbon atoms; and b is a number having a value from 0 to about 12. Preferred alkyl polyglycosides which can be used in the compositions according to the invention have the formula II wherein Z is or includes a glucose residue. Such alkyl polyglycosides are commercially available, for example; as TRITON® GC-100, an oligomer D-glucopyranose decyl octyl glycoside from Union Carbide Corporation, and APG®, GLUCOPON®, or PLANTAREN® surfactants from Cognis Corporation, Ambler, Pa. 19002. Examples of the Cognis surfactants include but are not limited to:

1. GLUCOPON® 225DK Surfactant—an alkyl polyglycoside in which the alkyl group contains 8 to 10 carbon atoms and having an average degree of polymerization of 1.7.
2. GLUCOPON® 425N Surfactant—an alkyl polyglycoside in which the alkyl group contains 8 to 16 carbon atoms, having an average of 10.3 carbon atoms, and having an average degree of polymerization of 1.5.
3. GLUCOPON® 625UP Surfactant—an alkyl polyglycoside in which the alkyl group contains 12 to 16 carbon atoms and having an average degree of polymerization of 1.6.
4. APG® 325N Surfactant—an alkyl polyglycoside in which the alkyl group contains 9 to 11 carbon atoms and having an average degree of polymerization of 1.5.
5. GLUCOPON® 600UP Surfactant—an alkyl polyglycoside in which the alkyl group contains 12 to 16 carbon atoms and having an average degree of polymerization of 1.4.
6. PLANTAREN® 2000 Surfactant—a $C_8$-$C_{16}$ alkyl polyglycoside in which the alkyl group contains 8 to 16 carbon atoms and having an average degree of polymerization of 1.5.
7. PLANTAREN® 1300 Surfactant—a $C_{12}$-$C_{16}$ alkyl polyglycoside in which the alkyl group contains 12 to 16 carbon atoms and having an average degree of polymerization of 1.6.
8. GLUCOPON® 220N Surfactant—an alkyl polyglycoside in which the alkyl group contains 8 to 10 carbon atoms and having an average degree of polymerization of 1.5.

Other examples of alkyl polyglycosides that can be used herein include alkyl polyglycoside surfactants which are comprised of mixtures of compounds of formula II wherein Z represents a moiety derived from a reducing saccharide containing 5 or 6 carbon atoms; b is a number having a value from 1 to about 6; and $R^1$ is an alkyl radical having from 8 to 20 carbon atoms. The compositions are characterized in that they have increased surfactant properties and an HLB in the range of about 10 to about 16 and a non-Flory distribution of glycosides, which is comprised of a mixture of an alkyl monoglycoside and a mixture of alkyl polyglycosides having varying degrees of polymerization of 2 and higher in progressively decreasing amounts, in which the amount by weight of polyglycoside having a degree of polymerization of 2 or mixtures thereof with the polyglycoside having a degree of polymerization of 3 predominate in relation to the amount of monoglycoside, said composition having an average degree of polymerization of about 1.8 to about 3. Such compositions, also known as peaked alkyl polyglycosides, can be prepared by separation of the monoglycoside from the original reaction mixture of alkyl monoglycoside and alkyl polyglycoside after removal of the alcohol. This separation may be carried out by molecular distillation and normally results in the removal of about 70-95% by weight of the alkyl monoglycosides. After removal of the alkyl monoglycosides, the relative distribution of the various components, mono- and poly-glycosides, in the resulting product changes and the concentration in the product of the polyglycosides relative to the monoglycoside increases as well as the concentration of individual polyglycosides to the total, i.e. DP2 and DP3 fractions in relation to the sum of all DP fractions. Such compositions are disclosed in U.S. Pat. No. 5,266,690, the entire contents of which are incorporated herein by reference.

In certain embodiments the formulation can include alkyl glycosides at concentrations of 0.5-1.0 wt %, 1-2 wt %, 2-3 wt %, 3-4 wt %, 4-5 wt %, 5-6 wt %, 6-7 wt %, 7-8 wt %, 8-9 wt %, 9-10 wt %, 10-11 wt %, 11-12 wt %, 12-13 wt %, 13-14 wt %, 14-15 wt %, 15-16 wt %, 16-17 wt %, 17-18 wt %, 18-19 wt %, 19-20 wt %, 20-21 wt %, 21-22 wt %, 22-23 wt %, 23-24 wt %, 24-25 wt %, 25-26 wt %, 26-27 wt %, 27-28 wt %, 28-29 wt % or 29-30 wt %, and any combination thereof with LMG, in the concentration noted herein above.

Other examples of surfactants that can be used herein include one or more nonionic polysorbate surfactants (polyoxyethylene fatty acid esters), obtained by the esterification of sorbitol with one or three molecules of a fatty acid, usually stearic, lauric, oleic, or palmitic acid, under conditions which cause splitting out of water from the sorbitol, leaving sorbitan fatty acid esters, i.e. a mixture of esters of the fatty acid with sorbitol and its mono- and di-anhydrides, and having a water content below 0.2%. The above ester mixture is then condensed with varying quantities of ethylene oxide, usually about 20 moles of ethylene oxide per mole of sorbitol. Examples of such polysorbate surfactants include, but are not limited to, Polysorbate 20 (polyoxyethylene (20) sorbitan monolaurate), Polysorbate 60 (polyoxyethylene (20) sorbitan monosterate), Polysorbate 80 (polyoxyethylene (20) sorbitan monooleate), Polysorbate 65 (polyoxyethylene (20) sorbitan tristearate), and Polysorbate 85 (polyoxyethylene (20) sorbitan trioleate).

In addition to the above polysorbate surfactants, surfactant sorbitan esters can also be used, either alone or in combination with a polysorbate. Sorbitan ester surfactants include sorbitan mono esters with fatty acid, preferably stearic, lauric, oleic, or palmitic acid.

The composition can be used by spray or direct manual application to the skin and hair.

Both the foregoing summary of the invention and the following detailed description of the invention are exemplary and explanatory and are intended to provide further details of the invention as claimed. Other objects, advantages, and novel features will be readily apparent to those skilled in the art from the following detailed description of the invention.

BRIEF DESCRIPTION OF THE DRAWING

The invention is described with reference to the following figures, which are presented for the purpose of illustration only and are not intended to be limiting of the invention.

DETAILED DESCRIPTION OF THE INVENTION

Figure 1:
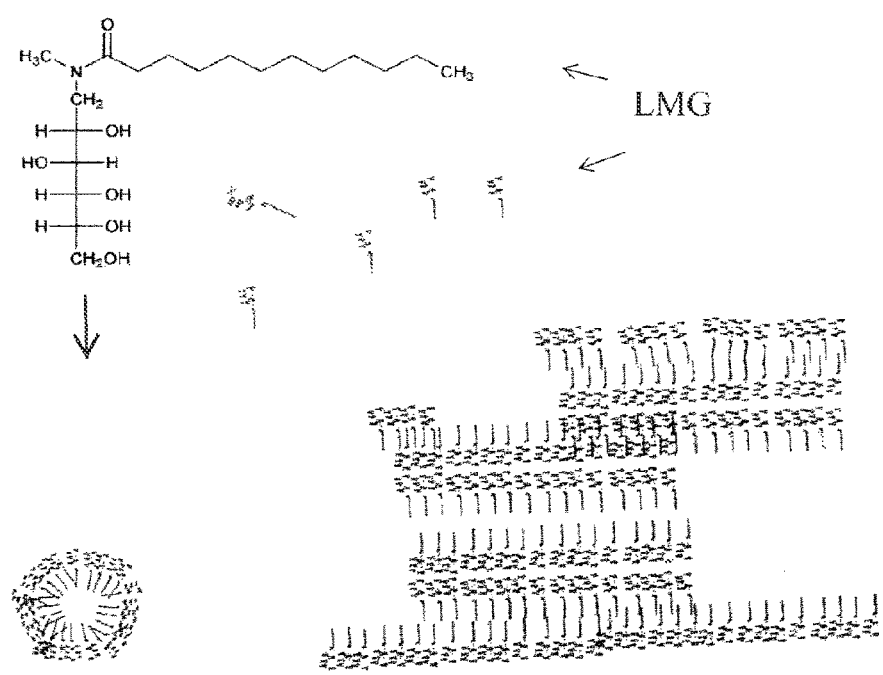
FIG. 1 is the chemical structure of Lauroyl N-Methyl Glucamide (LMG), along with cartooned drawings of the molecule to illustrate the structures of a micelle and an extended gel.

The present invention is directed to a simple method of formulating LMG for the purpose of its use on hair and skin surfaces, as a shampoo or skin cleanser/hydrating lotion. The method discloses the unanticipated property of LMG to form films on hair and skin that create a barrier to water loss. This type of barrier will reduce water loss from damaged or aging skin ("drying") or water absorption onto hair shafts ("frizzing"). Because LMG solidifies into a hard gel at the concentrations that are used for application to hair and skin, formulations are provided to prevent gel formation and at the same time permit the formation of that gel in skin and on hair to create the desired barrier. We disclose herein that by mixing specific concentrations of decyl glucoside with a desired concentration of LMG a concentrated solution of LMG can be formulated in such a way as to prevent its solidification at room temperature to facilitate its utility as a skin and hair care product. In addition, the formulation does not contain an ionic surfactant, nor any added salts, both of which negate the beneficial effects that are being sought. The formulation disclosed is a non-oily aqueous solution that imparts to the surface of skin or hair a water vapor barrier that compares in permeability to petrolatum, without the concomitant tactile sensations on skin.

Lauryl N-Methyl Glucamide as described in this invention is generally a mixture consisting of $C_{10}$, $C_{12}$, $C_{14}$, $C_{16}$ acyl compounds. It is waxy, non-oily solid that melts at about 60° C. in water. Prior art solutions of LMG are known to solidify into hard non-oily gels at temperatures below about 35° C. that resemble agar gels in feel and consistency.

The gel forming property of this water soluble compound suggested that LMG could be used to create a non-oily gel-based barrier on the surface of skin and hair. On the skin this non-oily barrier (or film) would be expected to reduce water vapor loss, due to its hydrophobic structure. On hair, the LMG barrier would be expected to provide a non-oily hydrophobic coating, reducing the adsorption of water vapor leading to "frizzing." In addition, the surfactant properties of LMG would impart a cleansing property to the formulation on skin and hair.

Skin and hair surfaces, composed of proteins, exhibit a negative and positive electrostatic charges, a consequence of the presence of free carboxylate moieties from glutamic and aspartic acid amino groups from lysine, and guanidino groups from arginine. A skin or hair product that contains ionic surfactants, or ionic organic molecules, will deposit these compounds on the surface of skin or hair as a consequence of the resulting electrostatic interactions between charged amino acid side chains of the proteins of skin and hair and the ionic components in the composition. This interaction will cause the organic components to be retained on the surface of the skin and hair, leaving behind a residue of these substances. These residues can interfere with the functionality of natural protective substances produced by the skin and scalp, such as antimicrobial peptides. Antimicrobial peptides are generally short cationic, amphipathic molecules. They are present on the surface of skin and released onto the growing hair shaft from cells within the follicle. Anionic surfactants, by virtue of their charge and amphipathic nature interact strongly with antimicrobial peptides and neutralize their activity. They are generally included to enhance the cleansing or foaming properties of the formulation. As an example, the shampoo disclosed in EP0550656B1 contains 3.5% LMG, but in addition 13.5% ammonium lauroyl sulfate, a strong anionic detergent. It would be desirable to avoid inactivating naturally occurring protective substances in a product designed to improve the health of skin and hair. Hence this invention discloses formulations that do not require the addition of ionic surfactants.

Similarly, the absence of salts, generally included as counter-ions to balance the charge on anionic surfactants or to increase the viscosity of solutions containing anionic surfactants, are not present or required in the disclosed formulations. These salts are necessarily deposited on skin and hair and are retained through ion exchange with naturally occurring ions. The naturally occurring antimicrobial agents deposited on hair and skin are most active in solutions at low ionic strength. Wetting the skin or hair with a solution containing salt would reduce the activity of these protective compounds, and thus interfere with their antimicrobial function. As an example, the shampoo disclosed in EP0550656B1 contains 3.5% LMG, but in addition 3% ammonium chloride and 0.6% ammonium citrate.

At 4° C. a 0.2 wt % solution of LMG in water forms a loose jelly-like solution. As the concentration of LMG increases the gels that are formed become increasingly more rigid, and the temperature at which the LMG solution gels, decreases progressively. The gelation property is reflection of the capacity of LMG to create extensive spatially extended networks in solution. For the purposes of use on hair and skin, concentrations of LMG of between 5-15 wt % are preferred, which form hard gels at about 35° C. An aqueous 15% solution of LMG would be solid at room temperature (21° C.) and would require heating to bring the formulation into solution.

The structure of the LMG (Formula I) molecule explains its gel forming property, it being comprised of a hydrophobic acyl tail and a hydrophilic linear carbohydrate. LMG does not appear to form stable micelles in aqueous solutions, since macroscopic aggregation occurs at concentrations far below the critical micelle concentration that occurs for other sugar lipid based surfactants. Gel formation may result from similar molecular dimensions of the hydrophobic and hydrophilic components of the LMG molecule which favors a side by side packing order rather than a spherical micelle configuration, and the hydrophobicity of the long chains which drives the hydrophobic aggregation, i.e. producing a layering of the molecules, representing an open packing array that can grow indefinitely (FIG. 1). The macroscopic gel formation can occur at very low concentrations, e.g. a 0.1% solution of N-Lauroyl-N-methyl glucamide heated to 45° C. will cool to form a physically stable gel having considerable volume and structural rigidity.

LMG is non-ionic, water soluble, and amphipathic, and as shares physical properties with molecules such as ceramides which can readily permeate the hair shaft and the stratum corneum of human and animal epidermis. Upon penetration into the intercellular matrix of the stratum corneum LMG would be expected to organize into the extended lamellar aggregates described above. These intradermal lamellar aggregates would improve the barrier properties of the epidermis, including epidermis deficient in the normal lipid barrier, which is known to occur in various disease states. On the surface of hair, a film containing LMG would be expected to organize into gelled barrier.

In addition, since LMG is a surfactant it is able to solubilize hydrophobic proteins and lipids normally resident on the hair and in the epidermis. These include proteins and lipids contained within lamellar bodies, which can undergo physical disruption, releasing diffusible contents which are then absorbed into the lipid/protein matrix that comprises the normal epidermal barrier. Thus the artificial barrier comprised of LMG would likely soon become populated by low molecular weight proteins and lipids normally resident on the surface of healthy hair and skin.

It would be advantageous for the purpose of skin and hair use to create an aqueous formulation of LMG which remains liquid at room temperature. As noted above a solution of LMG in water would cool to a solid at room temperature and would require heating to melt prior to use. In the present invention we disclose that by the addition of specific concentrations of an alkyl polyglycoside surfactant, preferably decyl glucoside, the temperature of the liquid-solid transition can be lowered. Furthermore, as we show herein, the application of this liquid formulation to skin and hair imparts a non-oily hydrophobic barrier.

Such surfactants include but are not limited to one or more sugar-based surfactants, i.e. alkyl polyglycosides. The alkyl polyglycosides have the formula (II) or Formula (III) below:

wherein $R_1$ is a monovalent organic radical having from about 6 to about 30 carbon atoms, preferably from 6 to 12 carbon atoms, and more preferably having an average of from 10 to 10.5 carbon atoms; Z is saccharide residue having 5 or 6 carbon atoms; and b is a number having a value from 0 to about 12. Preferred alkyl polyglycosides which can be used in the compositions according to the invention have the formula II wherein Z is or includes a glucose residue. Such alkyl polyglycosides are commercially available, for example; as TRITON® GC-100, an oligomer D-glucopyranose decyl octyl glycoside from Union Carbide Corporation, and APG®, GLUCOPON®, or PLANTAREN® surfactants from Cognis Corporation, Ambler, Pa. 19002. Examples of the Cognis surfactants include but are not limited to:

1. GLUCOPON® 225DK Surfactant—an alkyl polyglycoside in which the alkyl group contains 8 to 10 carbon atoms and having an average degree of polymerization of 1.7.
2. GLUCOPON® 425N Surfactant—an alkyl polyglycoside in which the alkyl group contains 8 to 16 carbon atoms, having an average of 10.3 carbon atoms, and having an average degree of polymerization of 1.5.
3. GLUCOPON® 625UP Surfactant—an alkyl polyglycoside in which the alkyl group contains 12 to 16 carbon atoms and having an average degree of polymerization of 1.6.
4. APG® 325N Surfactant—an alkyl polyglycoside in which the alkyl group contains 9 to 11 carbon atoms and having an average degree of polymerization of 1.5.

5. GLUCOPON® 600UP Surfactant—an alkyl polyglycoside in which the alkyl group contains 12 to 16 carbon atoms and having an average degree of polymerization of 1.4.
6. PLANTAREN® 2000 Surfactant—a $C_8$-$C_{16}$ alkyl polyglycoside in which the alkyl group contains 8 to 16 carbon atoms and having an average degree of polymerization of 1.5.
7. PLANTAREN® 1300 Surfactant—a $C_{12}$-$C_{16}$ alkyl polyglycoside in which the alkyl group contains 12 to 16 carbon atoms and having an average degree of polymerization of 1.6.
8. GLUCOPON® 220N Surfactant—an alkyl polyglycoside in which the alkyl group contains 8 to 10 carbon atoms and having an average degree of polymerization of 1.5.

Other examples of alkyl polyglycosides that can be used herein include alkyl polyglycoside surfactants which are comprised of mixtures of compounds of formula II wherein Z represents a moiety derived from a reducing saccharide containing 5 or 6 carbon atoms; b is a number having a value from 1 to about 6; and $R^1$ is an alkyl radical having from 8 to 20 carbon atoms. The compositions are characterized in that they have increased surfactant properties and an HLB in the range of about 10 to about 16 and a non-Flory distribution of glycosides, which is comprised of a mixture of an alkyl monoglycoside and a mixture of alkyl polyglycosides having varying degrees of polymerization of 2 and higher in progressively decreasing amounts, in which the amount by weight of polyglycoside having a degree of polymerization of 2 or mixtures thereof with the polyglycoside having a degree of polymerization of 3 predominate in relation to the amount of monoglycoside, said composition having an average degree of polymerization of about 1.8 to about 3. Such compositions, also known as peaked alkyl polyglycosides, can be prepared by separation of the monoglycoside from the original reaction mixture of alkyl monoglycoside and alkyl polyglycoside after removal of the alcohol. This separation may be carried out by molecular distillation and normally results in the removal of about 70-95% by weight of the alkyl monoglycosides. After removal of the alkyl monoglycosides, the relative distribution of the various components, mono- and poly-glycosides, in the resulting product changes and the concentration in the product of the polyglycosides relative to the monoglycoside increases as well as the concentration of individual polyglycosides to the total, i.e. DP2 and DP3 fractions in relation to the sum of all DP fractions. Such compositions are disclosed in U.S. Pat. No. 5,266,690, the entire contents of which are incorporated herein by reference.

Other examples of surfactants that can be used herein include one or more nonionic polysorbate surfactants (polyoxyethylene fatty acid esters), obtained by the esterfication of sorbitol with one or three molecules of a fatty acid, usually stearic, lauric, oleic, or palmitic acid, under conditions which cause splitting out of water from the sorbitol, leaving sorbitan fatty acid esters, i.e. a mixture of esters of the fatty acid with sorbitol and its mono- and di-anhydrides, and having a water content below 0.2%. The above ester mixture is then condensed with varying quantities of ethylene oxide, usually about 20 moles of ethylene oxide per mole of sorbitol. Examples of such polysorbate surfactants include, but are not limited to, Polysorbate 20 (polyoxyethylene (20) sorbitan monolaurate), Polysorbate 60 (polyoxyethylene (20) sorbitan monosterate), Polysorbate 80 (polyoxyethylene (20) sorbitan monooleate), Polysorbate 65 (polyoxyethylene (20) sorbitan tristearate), and Polysorbate 85 (polyoxyethylene (20) sorbitan trioleate).

In addition to the above polysorbate surfactants, surfactant sorbitan esters can also be used, either alone or in combination with a polysorbate. Sorbitan ester surfactants include sorbitan mono esters with fatty acid, preferably stearic, lauric, oleic, or palmitic acid.

Figure 2:
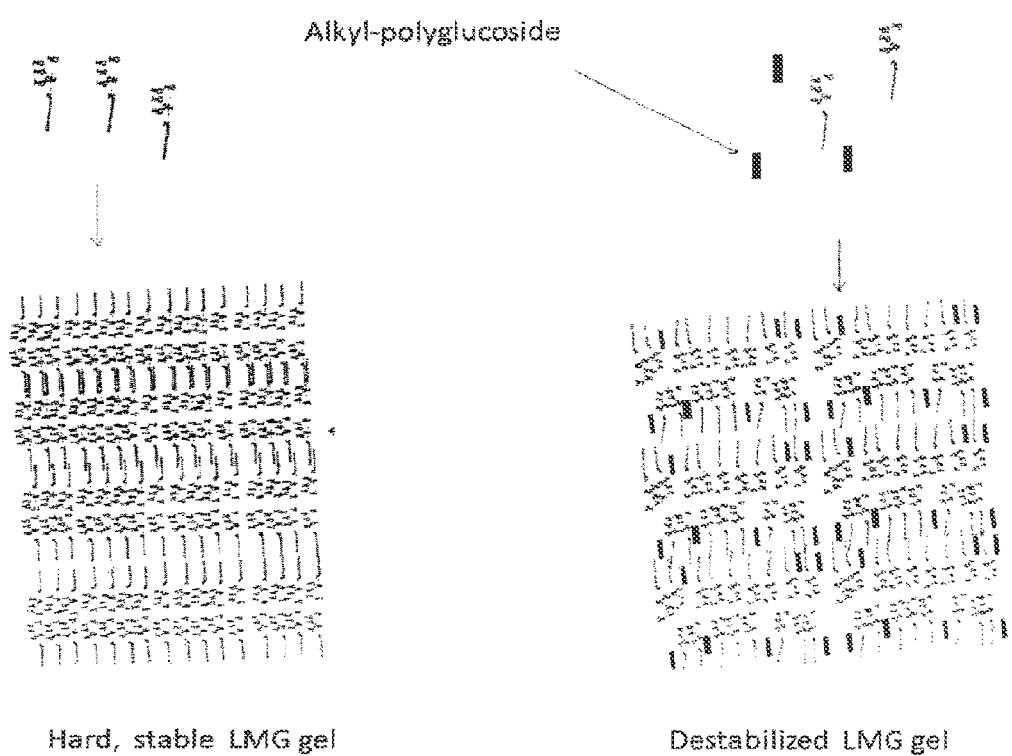
FIG. 2 is an illustration comparing the stable gel form of Lauroyl N-Methyl Glucamide (LMG) demonstrating the destabilizing effect of alkyl polyglucoside on the LMG gel.

Addition of decyl glucoside reduces the liquid-solid phase transition temperature of an LMG solution (see Example 1). This likely occurs due to the interspersion of the short chain alkyl sugar between the acyl chains of the LMG bilayer reducing the stability of the structure (FIG. 2). As the molar proportion of decyl glucoside relative to that of LMG increases, the LMG gel structure is progressively destabilized, reflected in the decreasing melting temperature of the LMG solid phase.

The solid structure destabilizing effects of decyl glucoside can be demonstrated in two ways: Firstly, on the temperature at which a solution of LMG solidifies; secondly, on the temperature at which an LMG solid melts. These two processes occur at different temperatures in the case of LMG. Thus, a 10 wt % solution of LMG solidifies at about 30° C., and melts, once formed, at about 50° C. (Table 1 and Example 1). If decyl glucoside is added to 0.5 wt %, the 10 wt % LMG solution solidifies at 30° C. and the solid, once formed, melts at 43° C. By progressively increasing the concentration of decyl glucoside to 5% and higher, the 10% LMG solution will not solidify as the temperature falls to −20° C., forming instead a "glass". As the temperature rises, the glass becomes less viscous (Table 1 and Example 1).

The present formulation of LMG disclosed herein will maintain a liquid physical state regardless of the temperatures to which the solution had been exposed, and regardless of the high concentration of this compound (10%). The disclosed formulation of LMG will remain liquid at room temperature or below. Thus, proportions of LMG and decyl glucoside can be adjusted specifically to insure that the formulation does not undergo a liquid to solid phase transition at low temperatures.

In contrast to the present invention, the prior art involving the use of LMG for direct use on hair or skin does not specifically teach how to avoid solidification at temperatures below ambient conditions. For example, the preferred composition of U.S. Pat. No. 6,395,258, which describes a hair mousse and shampoo, contains 8% LMG and 4% cocoamidylpropyl betaine as the principal components. When this formulation was prepared and then cooled, a hard solid formed at 15° C., and required heating to 31° C. to melt back into solution (Example 1).

Further, the disclosed formulation can be shown to exhibit barrier properties that reduce water loss from damaged skin (Example 3) and to impart volumizing effects on hair (Example 7).

In another embodiment of the invention the disclosed formulation can be mixed with other components to impart particular properties desired. These additives include non ionic or charged additives, one or more of those commonly present in cosmetics and other skin care products, such as viscosity modifiers, e.g. thickeners; propylene glycol; 1,3-butanediol; butylene glycol; ethanol; rheology modifiers, e.g. carbomers such as Carbopol® 940; emollients such as synthetic and natural esters, hydrocarbons such as petrolatum, mineral oil, isoparaffins, and hydrocarbon waxes such as polyethylene, starches, fatty acids, silicone oils such as cyclic or linear polydimethylsiloxanes, polyalkyl siloxanes, polyalkylarylsiloxanes, and polyether siloxane copolymers; hydroxyethyl cellulose; betaines; other alcohols such as stearyl alcohol and phenoxyethanol; perfumes; preservatives; other surfactants and soaps; and the like. In addition, water may be and usually is present as the remainder of the composition. The above list of skin care excipients is exemplary only and is not meant to be limiting. Examples of other surfactants that can be used are given below in a disclosure of the second embodiment of the invention.

The above compositions can also contain components having a therapeutic or protective effect on the skin, including OTC pharmaceuticals and other compounds having approved FDA monographs since the compositions enhance the absorption of such therapeutically active or protective compounds into the skin. Hence, conditions such as bacterial, viral, and fungal infections of the skin can be treated with the above compositions containing effective quantities of antiviral agents, antibiotics, antifungal agents, and mixtures thereof. Also, skin conditions requiring treatment with acne agents, analgesics, anorectal agents, scabicides, pediculicides, antineoplastics, antirosacea agents, acne treatment agents, antipruritics, antipsoriasis agents, depigmenting agents, topical hemostatics, wart treating agents, anti-itch agents, and the like can be treated using the compositions of the invention containing an effective quantity of one or more of the above active therapeutic compounds. Skin protective agents include antioxidants, antiaging actives, sun screening agents, and tanning agents. Preferred components having a therapeutic or protective effect on the skin are those having stability and efficacy over a broad pH range, e.g. between 4 and 8 or at least between 5 and 7. Here again the remainder of the compositions is usually water.

The compositions of the invention are useful as skin and hair care products, e.g., they are dermatologic external preparations for application to skin and hair. They can be used in the form of an aqueous solution and when skin care excipients are present they can be in the form of lotions, creams, astringents, facial packs, wrinkle-preventing eye creams, cleansing products to remove make-up, including theatrical make-up, and body care products such as shampoos, body cleansers, including powdered facial and body cleansers, and hand washers. They can also be used as peptizing agents for soap/syndet and syndet bar products. They form a gel-type film on the skin surface to maintain the lipid barrier properties of the skin, and to protect against trans epidermal water loss, and surprisingly are also absorbed into the stratum corneum producing a smooth silky feel to the skin, reducing dryness as well as reducing dermatitis, irritant dermatitis, and the like.

They also can be used to reduce the visible effects of aging and/or sun damage.

Owing to their lipid properties, the compositions of the invention help maintain the skin barrier function, reduce skin roughness, and provide a velvety skin after feel.

In addition, the disclosed formulations are nonirritating, mild to the skin and eyes, can provide good but not excessive lathering as skin cleansers, are substantive to the skin, spread easily, are nongreasy, are compatible with skin lipids, are odorless, are noncomedogenic, have an excellent shelf life, and are biodegradable.

The compositions of the invention are applied to the skin using known cosmetic applicators, or can be applied by hand. The compositions can be removed from the surface of the skin or left in place on the skin. The compositions should, however, be left in contact with the skin until the formula (I) compounds and other beneficial skin and hair care products, if present, have been absorbed into the stratum corneum or the shaft of the hair. This absorption usually takes place fairly rapidly, usually within 5 or 10 minutes.

It has further been discovered that the above compositions can restore the epithelial water barrier properties of damaged skin without needing to destroy or otherwise remove infectious microorganisms, including bacteria, fungi, viruses, and yeast from the skin, e.g. by counteracting the deleterious effects of hyphae produced by the mycelium of fungi that attacks the skin and its water barrier, such as Tinea pedis infections, commonly referred to as athlete's foot.

Hence the damaged skin can be restored without requiring the use of antibacterial, antiviral, and/or antifungal agents, which often have toxic or other deleterious side effects on the skin.

EXAMPLES

Example 1

A composition was prepared by dissolving 10% by weight of $C_{12}/C_{14}$ alkanoyl-N-methyl glucamide (wherein the $C_{12}$ and $C_{14}$ alkanoyl groups were obtained as a mixture from coconut oil), and 10% by weight glycerol in deionized water. The pH was then adjusted to 4-5 with HCl. Separate solutions were also prepared with increasing final concentrations of decyl glucoside: 0.0, 0.5, 1.0, 2.0, 3.0, 4.0, 5.0, 6.0. The compositions were brought into clear, colorless single phase solutions by heating to 60° C. The solutions were then cooled in a refrigerated chamber and the temperature at which gelling occurred was noted. As the concentration of decyl glucoside increased the temperature at which the LMG solution gelled decreased, forming a non-gelling glass at decyl glucoside concentrations of 5% and above. Thus the addition of decyl glucoside at concentrations of 5% or greater to a solution of 10% LMG and 10% glycerol prevents stable gel formation, even at temperatures as low as −20° C.

TABLE 3

| Decyl glucoside (wt %) | Temperature at which 10% LMG solution solidifies (° C.) |
|---|---|
| 0.0 | 35 |
| 0.5 | 30 |
| 1 | 25 |
| 2 | 21 |
| 3 | 4 |
| 4 | −8 |
| 5 | glass |
| 6 | glass |

The solids that had formed during the cooling of the solutions were then placed into a warming chamber and the temperature at which the solids melted were determined. In the absence of the addition of decyl glucoside, a solid containing 10% LMG and 10% glycerol melts at about 50° C. With increasing concentrations of decyl glucoside the melting temperature falls, such that at 5% and higher concentrations of decyl glucoside LMG does not solidify.

TABLE 4

| Decyl glucoside (wt %) | Temperature at which a 10% LMG solid melts (° C.) |
|---|---|
| 0.0 | 50 |
| 0.5 | 43 |
| 1 | 37 |
| 2 | 31 |
| 3 | 25 |
| 4 | 21 |
| 5 | glass |
| 6 | glass |

This example demonstrates that it is possible to formulate LMG with decyl glucoside to create a an LMG formulation that remains in a liquid phase at temperatures where LMG would necessarily solidify and require melting before use in the application to skin or hair.

A comparative example was prepared to demonstrate the effect of the formulation according to the present invention. Preferred formulations of LMG for use as a hair mousse and cleansers were disclosed in U.S. Pat. No. 6,395,258. Composition A was preferred:

TABLE 5

| | % (active ingredient) | | | | | | |
|---|---|---|---|---|---|---|---|
| | A | B | C | D | E | F | G |
| Amphomer | — | — | — | 1.2 | — | — | 1.2 |
| Sodium Polyvinyl Sulfonate | 0.6 | 0.6 | — | — | — | — | — |
| Shellac | — | — | 0.7 | — | — | — | — |
| Gantrez S97 (PVM/MA Copolymer)* | — | — | — | — | 0.4 | 0.7 | — |
| Amodimethicone | — | — | — | — | 0.5 | — | — |
| Coceth-10 | — | — | — | — | 5.0 | — | 5.0 |
| Undeceth-9 | — | — | — | — | — | 8.0 | — |
| Cocotrimonium chloride | 1.5 | 1.5 | 1.75 | — | 1.4 | 1.9 | 2.0 |
| N-Methyl C12/14 Alkyl Glucamide | 8.0 | 8.0 | 8.0 | 12.5 | — | — | — |
| Cocoamidopropyl betaine | 4.0 | 4.0 | 4.0 | 2.0 | 8.0 | 4.0 | 8.0 |
| Coco monoethanolamide | 1.0 | 1.0 | 1.0 | 2.0 | — | 1.0 | 2.0 |
| Sodium benzoate | 0.5 | 0.5 | 0.5 | 0.5 | 0.5 | 0.5 | 0.5 |
| Phenoxyethanol | 0.4 | 0.4 | 0.4 | 0.4 | 0.4 | 0.4 | 0.4 |
| PEG 6000 Distearate | — | 2.5 | — | — | — | — | — |
| Ethanol | — | — | 1.4 | — | — | — | — |
| Fragrance | 0.5 | 0.5 | 0.5 | 0.5 | 0.5 | 0.5 | 0.5 |
| Water | | | | to 100.0 | | | |

*Neutralized with amino methyl propanol.

Composition A was prepared as described in the above table.

At room temperature the solution was viscous in consistency. The solution solidified at 15° C. On standing at 0° C. for 1 hour it formed a hard waxy white gel that crumbled when penetrated with a probe. The resulting solid did not melt until the temperature increased to 35° C. Thus, it is evident that compositions that include LMG and other surfactants to achieve an optimal effect on hair or skin do not necessarily exhibit acceptable phase stability characteristics. Such phase transitions in a commercial product are unacceptable.

Example 2

A composition was prepared containing the following components:

| Component | % by weight | % by weight (active) |
|---|---|---|
| Water | 70.2 | |
| N-lauroyl-N-methyl-glucamide (70% active in water) | 3.74 | 2.62 |
| PLANTAREN ® 2000* (50% active in water) | 5.8 | 2.9 |
| PEG 150 distearate | 0.2 | 0.2 |
| Glycerin | 17 | 17.0 |

HCl (10%) to pH 6.15
*a $C_8$-$C_{16}$ alkyl polyglycoside having a degree of polymerization of 1.5.

The above formulation was prepared by adding the glycerin to the water with stirring until clear. Then the other components were added with stirring, and the resulting mixture was heated to 50° C. with stirring until clear. The pH was adjusted to 6.15 with the 10% HCl. The composition of Example 2 formed a viscous liquid at −20° C. which thinned to its original viscosity as the temperature was increased to room temperature.

Example 3

Repair of Epidermal Barrier as Measured by Trans-Epidermal Water Loss

Transepidermal water loss, the quantitative measurement of the evaporative loss of water across the epidermis, is a well-recognized measure of the integrity of the skin's hydrophobic barrier, a critical component of healthy skin structure.

The following clinical study presents a measurement of the kinetics of transepidermal water loss recovery in patients with atopic dermatitis, a skin condition associated with a damaged skin barrier, following application of various compositions to the skin surface.

Two subjects were enrolled in the study. The subjects were in general good health, with clinically verified atopic tendencies, as determined by a dermatologist, having compromised volar forearm skin, as determined by Baseline Dermalab readings of 4.0 or more on each arm. Individuals with active symptoms of allergy, atopic dermatitis, active eczema, active psoriasis, sunburn, excessive scarring, tattoos, or other skin condition in the test that would interfere with the assessments of this study as well as individuals with known allergies to lotions, moisturizers or other topical products were excluded from the study.

Transepidermal water loss (TEWL) were measured at Baseline (pre-composition application) and at 1, 2, 4 and 8 hours post-application.

In this study, the Dermalab, manufactured by Cortex Technologies, in conjunction with a computer, was used to measure TEWL utilizing an open chamber system.

A hand held probe placed on the skin surface sampled relative humidity at two points above the surface, allowing the rate of water loss to be calculated from the measured humidity gradient. Each TEWL measurement was taken over 60 seconds. Dermalab measurements were taken once on each test site at each time-point.

Prior to instrumental measurements, subjects rested quietly for at least 20 minutes in a designated room at a temperature of 66-74° F. and 15-55% relative humidity. Indoor temperature and humidity were recorded hourly during the course of the study visit.

Baseline TEWL measurements were taken on each test site. Test sites were demarcated with a surgical skin marker and were approximately 3 $cm^2$. The baseline Dermalab measurements were 4.0 or greater on each test site to qualify.

Qualified subjects gently washed the test sites with water and patted dry prior to composition application. Within 15 minutes of the wash, subjects had 20 micro-liters of test material applied to each test site, with one site left untreated. Test composition application was randomized on a site rotational basis. Subjects had Dermalab measurements repeated at approximately 1, 2, 4 and 8 hours post-application.

The compositions used in the study are as follows:
water
composition of Example 2
petrolatum (positive control)

Trans-epidermal water loss (TEWL) measurements were taken using the Dermalab at each test site prior to test material application (Baseline) and at 1, 2, 4, and 8 hours post-application. Table 2 presents the results of the TEWL measurements for each test material. Mean values at each post-application time point were statistically compared to mean Baseline values for significant differences. The average percent change from Baseline is listed in parentheses.

TABLE 6

MEAN VALUES FOR TEWL MEASUREMENTS (n = 2)

|  | Baseline (Pre-Application) | 1 Hour Post-Application | 2 Hours Post-Application | 4 Hours Post-Application | 8 Hours Post-Application |
|---|---|---|---|---|---|
| Water | 5.03 | 4.47 | 4.74 | 4.37 | 6.00 |
| Composition of Example 2 | 5.03 | 2.64 | 3.07 | 3.50 | 3.41 |
| Petrolatum - Positive Control | 4.67 | 1.91 | 2.30 | 3.00 | 3.06 |

From a statistical analysis of the mean TEWL values measured as a function of time after test formulation application, it is evident that Compositions of Example 2 cannot be distinguished from petrolatum with respect to repair of the TEWL property of atopic skin. In contrast, we can be 95% certain that water was less effective than petrolatum in this study.

TEWL values for normal healthy skin range between 2 and 3 ul/cm$^2$/hr. The baseline values for the patients included in this study ranged between 5.03 and about 6.7, indicative of skin with a damaged water barrier. Treatment with petrolatum resulted in a rapid and sustained improvement in the TEWL. The values achieved with petrolatum, between 1.9 (1 hr) rising to about 3 (8 hrs) represents the "normal" values characterizing this experimental setting. It is evident that the composition of Example 2 achieved normal or near normal TEWL values, comparable to petrolatum.

Example 4

A clinical trial was conducted to assess the efficacy to deliver and retain moisture to the skin after a single application of the composition of Example 2 by use of the Corneometer CM 825, the Skincon 200 EX. 8 subjects were enrolled. Each had mild to moderate dry skin on the lower legs. Measurements were taken in triplicate at baseline, 1 hour, 3 hours, and 6 hours post-application. The Corneometer quantifies the moisture content of the stratum corneum using an electrical capacitance method. The Skincon quantifies the moisture content using an electrical conductance method.

TABLE 7

|  |  | Pre-application | 1 hour post | 3 hours post | 6 hours post |
|---|---|---|---|---|---|
| Corneometer | Example 2 | 30.69 | 66.30* | 58.44* | 55.64* |
|  | No treatment | 29.56 | 33.25 | 32.32 | 34.88 |
| Skincon | Example 2 | 44 | 293* | 233* | 217* |
|  | No treatment | 42 | 50 | 49 | 48 |

*Statistically significant (p < 0.05) increase compared to baseline

This Example demonstrates that the formulation of Example 2 exhibits significant hydrating properties when applied to dry or damaged skin.

Example 5

Treatment of Tinea pedis infections with the composition of Example 2 compared to treatment with LAMISIL® cream.

Superficial fungal infections of the skin are amongst the most common infections in man. Current treatment universally involves administration of an antifungal compound applied locally to the affected skin site, or taken orally to provide systemic delivery. In addition, frequently fungal infections recur repeatedly on an infected site, requiring the repeated use of antifungal compounds, many of which have deleterious side effects.

The pathophysiology of the superficial infections caused by dermatophytes is reasonably well understood in its broad outlines. 1) Fungal organisms gain a foothold on the most superficial layers of skin; 2) The fungi secrete a broad range of hydrolytic enzymes including proteases and lipid degrading enzymes that damage the epidermal barrier; 3) The fungal products subsequently provoke inflammation as they penetrate the proliferative basal layer; and 4) hyper proliferation, associated with local inflammation, scaling, itching and secondary bacterial infection results.

A two-week clinical usage study was conducted with the composition of Example 2 and LAMISIL® cream. During the course of the study, subjects having a Tinea pedis infection, i.e. having a positive KOH test and the presence of athlete's foot on one or both feet, as determined by a score of 1 or greater for interdigital erythema and pruritus and/or burning/stinging, applied one of the following treatments as determined by a randomization design to a target foot selected by the study physician twice a day:
  Composition of Example 4—8 subjects
  LAMISIL® cream (OTC)—10 subjects
  Clinic evaluations were conducted at Baseline (Visit 1), Week 1 (Visit 2), and Week 2 (Visit 3). Subjects participated in the following procedures at the indicated visits:
Clinical Grading of Irritation Parameters: Baseline, Week 1, Week 2
The selected target lesion was clinically graded by the study physician for following parameters:
  Objective irritation (clinically graded): Erythema, Cracking/Fissuring, Scaling, and Pruritus
  Subjective irritation (assessed by subjects): Burning/Stinging
Target Foot Global Assessment: Week 1, Week 2
The study physician performed a global assessment of the target foot for the improvement of signs and symptoms.
Self-Assessment Questionnaire: Baseline, Week 1, Week 2
Subjects completed a Baseline self-assessment questionnaire regarding their perceptions of the severity of athlete's foot symptoms, including redness, pain, and interference with daily activities.
KOH Staining: Baseline, Week 2
The target area was scraped and transferred to a slide for potassium hydroxide (KOH) staining. The slide was examined to determine the presence of fungal hyphae.
Informed Consent
Written informed consent conforming to 21 CFR 50.25 was obtained from each subject prior to enrollment in the study.

Procedures and Methods

At Baseline (Visit 1), prospective subjects with self-perceived athlete's foot completed an Eligibility and Health Questionnaire and signed an Informed Consent Agreement and Confidentiality Agreement. The study physician (Board Certified Podiatrist) examined subjects' feet and selected a target foot and a target lesion on the selected foot to be tracked during the study. The location of the target lesion was marked on a body site map.

Subjects participated in the following Baseline/qualification procedures:

Clinical Grading

The selected target lesion was clinically graded by the study physician for following parameters using the indicated scales:
  Objective irritation (clinically graded): Erythema, Cracking/Fissuring, Scaling, Pruritus
  Subjective irritation (assessed by subjects): Burning/Stinging
    0=None
    1=Mild
    2=Moderate
    3=Severe
    (Half-point scores were used as necessary)

KOH Staining

The target area was scraped and transferred to a slide for potassium hydroxide (KOH) staining. The slide was examined to determine the presence of fungal hyphae.

Subjects qualified for study participation by having a positive KOH test and the presence of athlete's foot on one or both feet, as determined by a score of 1 or greater for interdigital erythema and pruritus and/or burning/stinging. Qualified subjects participated in the following procedures:

Self-Assessment Questionnaire

Subjects completed a Baseline self-assessment questionnaire regarding their perceptions of the severity of athlete's foot symptoms, including redness, pain, and interference with daily activities.

Subjects were assigned to one of the following treatments according to a pre-determined randomization design:

LAMISIL® Cream (OTC)

Composition of Example 2

Subjects were instructed to shower at least once daily and apply the assigned test material to both feet twice per day, each morning and prior to bedtime, as follows:

LAMISIL® Cream (OTC): Apply to affected areas of the foot as instructed by manufacturer.

Composition of Example 2

Apply three pumps of lotion to the affected foot.
Dispense lotion into the palm of cupped hand and work the liquid into the feet between the toes, on the sole, and around the sites of foot until entire foot is covered with lotion.
Let feet dry for at least five minutes prior to covering feet (with socks, shoes, hosiery, bed sheets, etc.).

Subjects were provided with written usage instructions, a calendar of study visits, and a daily diary to record test material application times and comments.

Subjects returned to the clinic at Week 1 (Visit 2) and Week 2 (Visit 3). Subjects participated in the following procedures at each visit as indicated:

Daily diaries were reviewed for compliance and subjects were questioned regarding changes in their health status and medications.

Subjects completed a self-assessment questionnaire regarding the severity of athlete's foot symptoms.

The study physician graded subject's selected target lesion for objective and subjective irritation parameters as described for Baseline.

The study physician also performed a global assessment of the target foot using the following scale:
  1=Clear: 100% remission of clinical signs and symptoms
  2=Excellent: 80-99% improvement from Baseline
  3=Good: 50-79% improvement from Baseline
  4=Fair: 25-49% improvement form Baseline
  5=Poor: less than 25% improvement from Baseline
  6=Worse: clinical signs and symptoms worse than Baseline At Week 2 only, the target lesion was scraped and transferred to a slide for KOH staining, which was examined to confirm the presence of fungal hyphae.

Subjects returned completed diaries and test material units to the clinic at the completion of Visit 3. Test material units were weighed for compliance.

Biostatistics and Data Management

Mean values for clinical grading parameters and self-assessment questionnaires at Week 1 and Week 2 were statistically compared to mean Baseline values using a paired t-test at the $p \leq 0.05$ significance level. Mean percent change and incidence of improvement were calculated for all attributes. Comparisons were made among the three treatments using analysis of variance (ANOVA) with paired comparisons (Fisher's LSD). Results for target foot global assessment grading at Week 1 and Week 2, and for KOH staining at Week 2 were tabulated and a top box analysis was performed. Fisher's Exact Test (2-sided) was used to determine between treatment comparisons.

Results

At Baseline, Week 1, and Week 2, the selected target lesion was clinically graded for objective and subjective irritation parameters. Table 8 presents the results of the clinical grading for each treatment. Mean values at Week 1 and Week 2 are statistically compared to mean Baseline values. The average percent change from Baseline is listed in parentheses.

TABLE 8

MEAN VALUES FOR CLINICAL GRADING OF TARGET LESION IRRITATION PARAMETERS

| | | Baseline (Visit 1) | Week 1 (Visit 2) | Week 2 (Visit 3) |
|---|---|---|---|---|
| LAMISIL ® Cream (OTC) (n = 10) | Erythema | 0.75 | 0.35 (−53.3%) | 0.45 (−40.0%) |
| | Crackling/Fissuring | 0.70 | 0.35 (−50.0%) | 0.30 (−57.1%) |
| | Scaling | 1.05 | 1.25 (19.0%) | 0.85 (−19.0%) |
| | Pruritus | 2.00 | 0.45* (−77.5%) | 0.20* (−90.0%) |
| | Burning/Stinging | 1.55 | 0.40* (−74.1%) | 0.00* (−100%) |
| Composition of Example 2 | Erythema | 1.25 | 1.00 (−20.0%) | 0.69 (−45.0%) |
| | Crackling/Fissuring | 0.69 | 0.63 (−9.0%) | 0.31 (−54.5%) |
| | Scaling | 1.06 | 0.81 (−23.5%) | 0.69* (−35.2%) |
| | Pruritus | 2.13 | 1.00* (−52.9%) | 0.31* (−85.2%) |
| | Burning/Stinging | 1.00 | 0.31* (−68.7%) | 0.19* (−81.2%) |

*Indicates a statistically significant ($p \leq 0.05$) decrease (improvement) compared to Baseline Results of ANOVA Comparisons for Irritation Grading Comparisons based on the average change from Baseline, were made among the two treatments for irritation parameter grading. Results of the comparisons showed no statistically significant ($p \leq 0.05$) differences among the three treatments for any graded objective or subjective irritation parameter.

At Week 1 and Week 2, the study physician performed a global assessment of the target foot. The Table below presents the results of the target foot global assessment for each treatment. The number and percentage of subjects with each score is presented, and the p-value indicating statistical significance between the positive and negative scores is also listed.

TABLE 9

RESULTS OF TABULATIONS FOR TARGET FOOT GLOBAL ASSESSMENTS

| | LAMISIL ® Cream (OTC) (n = 10) | | Composition of Example 2 (n = 8) | |
|---|---|---|---|---|
| | Week 1 | Week 2 | Week 1 | Week 2 |
| 1 = Clear: 100% remission of clinical signs and symptoms | 0 (0.0%) | 1 (10.0%) | 0 (0.0%) | 1 (12.5%) |
| 2 = Excellent: 80-99% improvement from Baseline | 2 (20.0%) | 4 (40.0%) | 1 (12.5%) | 3 (37.5%) |
| 3 = Good: 50-79% improvement from Baseline | 2 (20.0%) | 4 (40.0%) | 3 (37.5%) | 1 (12.5%) |
| 4 = Fair: 25-49% improvement from Baseline | 5 (50.0%) | 0 (0.0%) | 2 (25.0%) | 3 (37.5%) |
| 5 = Poor: less than 25% improvement from Baseline | 0 (0.0%) | 1 (10.0%) | 2 (25.0%) | 0 (0.0%) |
| 6 = Worse: clinical signs and symptoms worse than Baseline | 1 (10.0%) | 0 (0.0%) | 0 (0.0%) | 0 (0.0%) |
| Positive Grades: Score of 1, 2, 3 | 4 (40.0%) | 9 (90.0%) | 4 (50.0%) | 5 (62.5%) |
| Negative Grades: Score of 5 and 6 | 1 (10.0%) | 1 (10.0%) | 2 (25.0%) | 0 (0.0%) |
| p-value: | 0.180 | 0.011 | 0.414 | 0.025 |

A significantly greater proportion of subjects received a positive score (1, 2, 3) than negative score (5, 6) for LAMISIL® Cream and the Composition of Example 8 at Week 2.

Results of Comparisons for Target Foot Global Assessment

Fisher's Exact Test (2-sided) was used for between treatment comparisons between positive and negative grades. Results of the comparisons showed no statistically significant differences between the two treatments for target foot global assessment at Week 1 and Week 2.

At Baseline, Week 1, and Week 2, subjects completed a self-assessment questionnaire regarding their perceptions of the severity of their athlete's foot symptoms using the following scales:

TABLE 10

| | 0 | 3 | 6 | 9 |
|---|---|---|---|---|
| 1. What is the severity of your athlete's foot symptoms | Not at all | Mild | Moderate | Severe |
| 2. How red and inflamed (overall, on average) do you feel your condition is | | | | |
| 3. How painful/uncomfortable are your symptoms | Not at all | Somewhat | Moderately/ Fairly | Extremely |
| 4. Do you feel this condition interferes with your daily activities | | | | |

The Table below presents the results of the self-assessment questionnaire analysis for each treatment. Mean values at Week 1 and Week 2 are statistically compared to mean Baseline values. The average percent change from Baseline is listed in parentheses.

TABLE 11

MEAN VALUES FOR SELF-ASSESSMENT QUESTIONNAIRES

| | | Baseline (Visit 1) | Week 1 (Visit 2) | Week 2 (Visit 3) |
|---|---|---|---|---|
| LAMISIL ® Cream (OTC) (n = 10) | 1. Severity of symptoms | 5.30 | 4.20* (−20.7%) | 3.10* (−41.5%) |
| | 2. Red and inflamed | 5.20 | 3.10* (−40.3%) | 2.60* (−50.0%) |
| | 3. Painful/uncomfortable | 4.80 | 2.60* (−45.8%) | 2.00* (−58.3%) |
| | 4. Daily activities interference | 3.50 | 1.60* (−54.2%) | 1.70 (−51.4%) |
| Composition of Example 4 | 1. Severity of symptoms | 6.00 | 4.38* (−27.0%) | 2.88* (−52.0%) |
| | 2. Red and inflamed | 5.50 | 3.13* (−43.1%) | 2.63* (−52.2%) |
| | 3. Painful/uncomfortable | 4.75 | 3.00* (−36.8%) | 2.00* (−57.8%) |
| | 4. Daily activities interference | 4.25 | 2.63* (−38.2%) | 2.25 (−47.0%) |

*Indicates a statistically significant ($p \leq 0.05$) decrease (improvement) compared to Baseline.

Results of ANOVA Comparisons for Self-Assessment Questionnaires

Comparisons, based on the average change from Baseline, were made among the two treatments for self-assessment questions. Results of the comparisons showed no statistically significant (p≤0.05) differences among the two treatments for any of the self-assessment questions.

At Baseline and Week 2, the target area of each subject was scraped and transferred to a slide for potassium hydroxide (KOH) staining, and the slide was examined to determine the presence of fungal hyphae. All subjects tested positive for KOH staining at Baseline in order to qualify for the study. The Table below presents the results of the KOH staining at Week 2. The number and percentage of subjects with a positive and negative stain is presented, and the p-value indicating statistical significance between the positive and negative stain percentages is also listed.

TABLE 12

RESULTS OF TABULATIONS FOR KOH STAINING AT WEEK 2

|  | LAMISIL® Cream (OTC) (n = 10) | Composition of Example 4 (n = 8) |
|---|---|---|
| Positive (+) | 1 (10.0%) | 6 (75.0%) |
| Negative (−) | 9 (90.0%) | 2 (25.0%) |
| p-value | 0.11 | 0.157 |

A significantly greater proportion of subjects had a negative stain than a positive stain for LAMISIL® Cream at Week 2.

Results of Comparisons for KOH Staining at Week 2

Fisher's Exact Test (2-sided) was used for between treatment comparisons between positive and negative stains. Results of the comparisons showed that there was a statistically significant (p=0.012) difference between the two treatments for KOH staining Discussion and Conclusions The following table shows the statistically significant decreases (improvements) compared to Baseline for each test treatment:

TABLE 13

|  | LAMISIL® Cream (OTC) (n = 10) | | Composition of Example 2 (n = 8) | |
|---|---|---|---|---|
|  | Week 1 | Week 2 | Week 1 | Week 2 |
| Erythema | | | | |
| Crackling/Fissuring | | | | |
| Scaling | | | | * |
| Pruritus | * | * | * | * |
| Burning/Stinging | * | * | * | * |

* Indicates a statistically significant (p ≤ 0.05) decrease (improvement) compared to Baseline.

Comparisons between the two treatments showed no statistically significant differences for clinical grading of target lesion irritation parameters.

Target Foot Global Assessment

At Week 1 and Week 2, the study physician performed a global assessment of the target foot for the improvement of signs and symptoms compared to Baseline. Results of the tabulations for target foot global assessment showed that a significantly greater proportion of subjects received a positive score (1, 2, 3) than negative score (5, 6) for LAMISIL® Cream and for the Composition of Example 2 at Week 2. Comparisons among the two treatments showed no statistically significant differences between positive and negative scores for target foot global assessment.

Self-Assessment Questionnaire

At Baseline, Week 1, and Week 2, subjects completed a Baseline self-assessment questionnaire regarding their perceptions of the severity of athlete's foot symptoms, including redness, pain, and interference with daily activities. Results of the self-assessment questionnaire analysis showed a statistically significant decrease (improvement) in the following questions at the indicated time points for each treatment:

TABLE 14

|  | LAMISIL® Cream (OTC) | | Composition of Example 2 | |
|---|---|---|---|---|
|  | Week 1 | Week 2 | Week 1 | Week 2 |
| 1. Severity of symptoms | * | * | * | * |
| 2. Red and inflamed | * | * | * | * |
| 3. Painful/uncomfortable | * | * | * | * |
| 4. Daily Activities | * | | * | |

* Indicates a statistically significant (p ≤ 0.05) decrease (improvement) compared to Baseline.

Comparisons among the two treatments showed no statistically significant differences for self-assessment questions.

KOH Staining

At Baseline and Week 2, the target area was scraped and transferred to a slide for KOH staining. The slide was examined to determine the presence of fungal hyphae. All subjects tested positive for KOH staining at Baseline in order to qualify for the study. At Week 2, a significantly greater proportion of subjects had a negative stain than positive stain for LAMISIL® Cream. Results of the comparisons among the two treatments showed that there was a statistically significant (p=0.012) difference for KOH staining It is clear from this study that the formulation of Example 2 achieved clinical improvements and resolution of confirmed T. pedis infections comparable to LAMISIL® cream, a commercial product. Despite the modest reduction in the presence of dermatophytes, clinical benefit was observed, suggesting that the dermatophytes were now simply colonizing the skin rather than behaving as pathogens. Since the composition of Example 2 possesses little or no antimicrobial activity nor activity against dermatophytes, the clinical resolution of the T. pedis infection must have occurred through a secondary effect on the skin itself, i.e. the compositions of this embodiment create a hydrophobic gel barrier within the stratum corneum, thus physically separating the microbes and their noxious products from the underlying skin tissues. Standard hydrophobic creams coat the superficial layers of the skin, thus sealing the microbes within the barrier.

Example 6

A composition was prepared containing the following components:

| Component | % by weight (active) |
|---|---|
| Water | 48 |
| LMG (96% active in water) | 14 |
| PLANTAREN® 2000* (50% active in water) | 25 |
| PEG 150 distearate | 0.9 |
| Glycerin | 12 |
| HCl to pH 6.0 | 1 |

Example 7

A composition of Example 6 was placed into a −20° C. freezer, and within several hours formed a glass. Warming to room temperature restored the liquid to its original viscosity.

The composition was applied as a shampoo to wet hair. The composition lathered well. The composition did not remove coloring dye from treated hair. After drying the hair was noticeably soft and lustrous. Exposure of the washed and dried hair to steam vapor did not cause frizzing, suggesting that a water barrier had been imparted to the hair shafts. Continued weekly use over the course of several weeks appeared to reduce hair breakage and hair loss.

What is claimed is:

1. A liquid composition that is free of ionic surfactants and salts for use as a shampoo or skin cleanser/hydrating lotion consisting essentially of an aqueous formulation of C12/C14 alkanoyl-N-methyl-glucamide (LMG) at a concentration between 0.5% and 30% by weight and decyl glucoside at a concentration between 0.5% and 60% by weight, with the weight ratio of the two compounds LMG and decyl glucoside between 2:1 and 1:3, and which remains liquid at temperatures below 0° C.

2. The composition of claim 1, wherein C12/C14 alkanoyl-N-methyl-glucamide is at a concentration between 0.5% and 30% by weight and decyl glucoside is at a concentration between 0.5% and 30% by weight, with the weight ratio of the two compounds LMG and decyl glucoside between 2:1 and 1:1, and which remains liquid at temperatures below 0° C.

3. The composition of claim 1, wherein the composition contains one or more additives to improve viscosity, fragrances, preservatives, silicones, essential oils, conditioners, and therapeutic agents, in order to impart desired additional properties to the compositions.

4. A method of fortifying or repairing the epidermal water barrier of animal skin comprising applying to the animal skin on effective quantity of the composition of claim 1.

5. The method of claim 4, wherein the animal is human.

6. The method of claim 5, wherein the human skin is infected with a fungus infection.

7. A method of fortifying or repairing the water barrier of hair comprising applying to the animal skin on effective quantity of the composition of claim 1.

8. The method of claim 7, wherein the animal is human.

9. The method of claim 8, wherein the human skin is infected with a fungus infection.

\* \* \* \* \*